United States Patent
Scott et al.

(10) Patent No.: US 11,549,151 B2
(45) Date of Patent: **\*Jan. 10, 2023**

(54) SYSTEMS AND METHODS FOR PROVIDING PERSONALIZED RADIATION THERAPY

(71) Applicant: H. LEE MOFFITT CANCER CENTER AND RESEARCH INSTITUTE, INC., Tampa, FL (US)

(72) Inventors: Jacob Scott, Tampa, FL (US); Javier F. Torres-Roca, St. Petersburg, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/900,242

(22) Filed: Jun. 12, 2020

(65) Prior Publication Data
US 2020/0308658 A1 Oct. 1, 2020

Related U.S. Application Data

(63) Continuation of application No. 15/571,617, filed as application No. PCT/US2016/031038 on May 5, 2016, now Pat. No. 10,697,023.
(Continued)

(51) Int. Cl.
*A61N 5/10* (2006.01)
*C12Q 1/6886* (2018.01)
(Continued)

(52) U.S. Cl.
CPC ......... *C12Q 1/6886* (2013.01); *A61N 5/1031* (2013.01); *C12Q 1/68* (2013.01);
(Continued)

(58) Field of Classification Search
CPC .. A61N 5/103–1039; A61N 5/10–1084; A61N 5/1041; A61N 5/1085–1098
See application file for complete search history.

(56) References Cited

U.S. PATENT DOCUMENTS 7,819,847 B2 10/2010 Vitello et al.
8,660,801 B2 2/2014 Torres-Roca et al.
(Continued)

FOREIGN PATENT DOCUMENTS

CN 101043905 A 9/2007
CN 102481342 A 5/2012

OTHER PUBLICATIONS

International Search Report and Written Opinion in PCT Application No. PCT/US2016/031038, dated Aug. 11, 2016.
(Continued)

*Primary Examiner* — Thaddeus B Cox
(74) *Attorney, Agent, or Firm* — Meunier Carlin & Curfman LLC

(57) ABSTRACT

An example method of treating a subject having a tumor is described herein. The method can include determining a radiosensitivity index of the tumor, deriving a subject-specific variable based on the radiosensitivity index, and obtaining a genomic adjusted radiation dose effect value for the tumor. The radiosensitivity index can be assigned from expression levels of signature genes of a cell of the tumor. Additionally, the genomic adjusted radiation dose effect value can be predictive of tumor recurrence in the subject (Continued)

after treatment. The method can also include determining a radiation dose based on the subject-specific variable and the genomic adjusted radiation dose effect value.

22 Claims, 10 Drawing Sheets

Related U.S. Application Data

(60) Provisional application No. 62/157,245, filed on May 5, 2015.

(51) Int. Cl.
    *G16B 25/00*     (2019.01)
    *G16B 40/00*     (2019.01)
    *C12Q 1/68*     (2018.01)
    *G16H 20/40*     (2018.01)
    *G16B 25/10*     (2019.01)

(52) U.S. Cl.
    CPC ............. *G16B 25/00* (2019.02); *G16B 25/10* (2019.02); *G16B 40/00* (2019.02); *G16H 20/40* (2018.01); *A61N 2005/1032* (2013.01); *C12Q 2600/106* (2013.01); *C12Q 2600/158* (2013.01)

(56) References Cited

U.S. PATENT DOCUMENTS

| | | | |
|---|---|---|---|
| 2006/0084666 | A1 | 4/2006 | Harari et al. |
| 2011/0112016 | A1 | 5/2011 | Barnea |
| 2012/0004492 | A1 | 1/2012 | Weibrecht et al. |
| 2012/0183536 | A1 | 7/2012 | Evans-Freke |
| 2014/0336945 | A1 | 11/2014 | Torres-Roca et al. |
| 2014/0363816 | A1 | 12/2014 | Theodorescu et al. |
| 2016/0008629 | A1 | 1/2016 | Ribbing et al. |
| 2016/0054337 | A1 | 2/2016 | Azria et al. |
| 2016/0146819 | A1 | 5/2016 | Ince |
| 2019/0022411 | A1 | 1/2019 | Parry et al. |

OTHER PUBLICATIONS

Torres-Roca, J., "A Molecular Assay of Tumor Radiosensitivity: A Roadmap Towards Biology-based Personalized Radiation Therapy," Personalized Medicine, Jul. 2012, vol. 5, No. 5, pp. 1-17.

Extended European Search Report issued in EP16790104 dated Dec. 4, 2018 (8 pages).

Sunirmal Paul et al., "Prediction of In Vivo Radiation Dose Status in Radiotherapy Patients using Ex Vivo and In Vivo Gene Expression Signatures," Radiation Research, vol. 175, No. 3, Mar. 1, 2011, pp. 257-265.

J. Kritz et al., "Comparison Between the German Hodgkin Study Group (GHSG) Invovled Field Radiation Therapy (IF-RT) Versus the International Lymphoma Radiation Oncology Group (ILROG) Involved Site Radiation Therapy (IS-RT) for Patients with Hodgkin Lymphoma—Is ISRT the New Standard?", International J. of Radiation: Oncology Biology Physics., vol. 90, No. 1, Sep. 1, 2014, p. S153.

Speers et al., "Development and Validation of a Novel Radiosensitivity Signature in Human Breast Cancer", Clin. Cancer Res. 2015, vol. 21, p. 3667-3677 (Apr. 22, 2015).

Communication Pursuant to Article 94(3) EPC, issued for Application No. 16790104.0, dated Nov. 2, 2020.

Strom, TJC., et al. "Genomically adjusted radiation dose to predict for survival with adjuvant radiation in resectable pancreatic cancer." (2016): 240.

Ahmed, K., et al. "Utilizing the Genomically Adjusted Dose (Gad) To Identify Patients For Adjuvant Radiation Dose Escalation In Glioblastoma." Neuro-oncology 17.Suppl 5 (2015): v195-V200.

Jeong, J., et al., "Modelling the interplay between hypoxia and proliferation in radiotherapy tumour response." Physics in Medicine & Biology 58.14 (2013): 4897-4919.

Altobelli, E., et al., "HtrA1 as a promising tissue marker in cancer: a meta-analysis." BMC cancer 18.1 (2018): 1-9.

Examination Report No. 1 issued for Australian Application No. 2016259007, dated Jul. 14, 2021.

Office Action issued for Chinese Application No. 201680031620.9, dated Apr. 16, 2021.

Office Action, dated May 19, 2022, received in connection with corresponding CA Patent Application No. 2,984,789.

GENOMICALLY GUIDED RADIATION THERAPY

| COHORT | MEDIAN F/U (MONTHS) | RT DOSE RANGE (GY) | GAD RANGE | ENDPOINT | UVA | P | MVA | P |
|---|---|---|---|---|---|---|---|---|
| BREAST (n=77) | 72 | 50 | 8-60 | RFS | 7.6 (1.6-136) | 0.007 | 7.4 (1.4-138) | 0.01 |
| BREAST (n=263) | 60 | 45-71 | 4-104 | DMFS | 2.3 (1.3-4.3) | 0.007 | 2.1 (1.1-3.9) | 0.02 |
| BREAST (n=75) | 120 | 45-55 | 9-37 | LC | 2.8 (1.3-6.3) | 0.007 | 3.4 (1.3-9.7) | 0.01 |
| LUNG (n=60) | 46 | 45-70 | 15-125 | LC | 1.9 (1.1-3.1) | 0.02 | 1.9 (1.1-3.1) | 0.02 |
| GBM (n=98) | 11 | 12.6-97 | 0.4-46 | OS | 2.4 (1.2-4.9) | 0.02 | 3.2 (1.5-6.6) | 0.004 |
| PANCREAS (n=40) | 68 | 45-54 | 16-40 | OS | 1.3 (0.6-2.8) | 0.48 | 2.6 (1.1-6.0) | 0.03 |

FIG. 5

| Multivariate Analysis of GARD | | | |
|---|---|---|---|
| Parameter (Reference) | Level | Hazard Ratio | P Value |
| GARD (GARD ≥ Q4) | GARD < Q3 | 2.11 (1.13, 3.94) | 0.01 |
| ER_PR (ER+/PR+) | ER+/PR- or ER-/PR+ | 1.28 (0.76, 2.17) | 0.35 |
| ER_PR | ER-/PR- | 0.98 (0.57, 1.68) | 0.93 |
| T_Stage (T stage = T1) | T2, T3, or T4 | 1.36 (0.86, 2.16) | 0.18 |
| age (Ref age ≤ 40) | 41-55 | 0.78 (0.42, 1.43) | 0.41 |
| age | 56-70 | 0.84 (0.44, 1.59) | 0.59 |
| age | 71-83 | 0.37 (0.12, 1.13) | 0.08 |
| surgery | Lumpectomy | 1.97 (0.88, 4.43) | 0.1 |

FIG. 9

SYSTEMS AND METHODS FOR PROVIDING PERSONALIZED RADIATION THERAPY

CROSS-REFERENCE TO RELATED APPLICATIONS

This application is a continuation of U.S. Patent Application No. 15/571,617, filed Nov. 3, 2017, now U.S. Pat. No. 10,697,023, which is a national stage application filed under 35 U.S.C. § 371 of PCT/US2016/031038, filed on May 5, 2016, which claims the benefit of U.S. provisional patent application No. 62/157,245, filed on May 5, 2015, and entitled "SYSTEMS AND METHODS FOR PROVIDING PERSONALIZED RADIATION THERAPY," the disclosures of which are expressly incorporated herein by reference in their entireties.

STATEMENT REGARDING FEDERALLY FUNDED RESEARCH

This invention was made with government support under Grant no. CA101355 and CA135620 awarded by the National Institutes of Health and Grant no. DAMD17-02-2-0051 awarded by the US Army Medical Research and Materiel Command (ARMY/MRMC). The government has certain rights in the invention.

BACKGROUND

Radiation Therapy (RT) is a highly utilized, efficacious and cost-effective therapeutic option for cancer patients. RT is received by up to two-thirds of all cancer patients in the US, has been estimated to be responsible for 40% of all cancer cures, yet represents only 5-10% of all cancer-related health expenditures[1,2]. In spite of its therapeutic importance, it is under-represented in the national portfolio of clinical trials (i.e. only 5.5% of NCI trials involve RT)[2].

The sequencing of the human genome has paved the way for the era of precision medicine which promises that the right treatment will be delivered to the right patient at the right time. While the genomic era has affected the delivery of chemotherapy and targeted biological agents[3][4][5], it has yet to impact RT, the single most utilized therapeutic agent in oncology[6].

A central principle in precision medicine is that cancer therapy should be tailored to individual tumor biology[7][8][9]. In spite of this tenet, RT dose protocols are uniform or one-size-fits-all (e.g., a uniform daily dose rate of 2 Gray ("Gy")) and have not yet been adapted to this vision. Thus, integrating individual biological differences into RT protocols is a central step towards realizing the promise of precision medicine, thereby improving RT-based clinical outcomes. Previously, a gene-expression based radiosensitivity index (RSI) was developed that has been validated in over 2,000 patients as a predictor of clinical outcome in RT-treated patients in multiple independent cohorts and disease sites[10-19]. These data support that clinical benefit from RT is non-uniform and only maximized in a subpopulation of genomically-distinct patients (e.g. radiosensitive).

Personalized RT holds the promise that the diagnosis, prevention, and treatment of cancer can be based on individual assessment of risk.

SUMMARY

Systems and methods for providing personalized radiation therapy are described herein. For example, a radiosensitivity index ("RSI"), which is a molecular signature derived from cellular survival, can be used to customize radiation therapy for an individual subject. RSI can optionally be used to prescribe (and optionally administer) a personalized radiation dose to the subject. For example, using the RSI, a particular radiation dose per treatment and/or a particular number of radiation therapy treatments (or fractionation) can be prescribed for (and optionally administered to) the subject in order to reduce the likelihood of tumor reoccurrence after radiation treatment.

An example method of treating a subject having a tumor is described herein. The method can include determining a radiosensitivity index of the tumor, deriving a subject-specific variable based on the radiosensitivity index, and obtaining a genomic adjusted radiation dose effect value for the tumor. The radiosensitivity index can be assigned from expression levels of signature genes of a cell in the tumor. The signature genes can include, but are not limited to, Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); and/or Interferon regulatory factor 1 (IRF1). Additionally, the genomic adjusted radiation dose effect value can be predictive of tumor recurrence in the subject after treatment. The method can also include determining a radiation dose based on the subject-specific variable and the genomic adjusted radiation dose effect value. The radiation dose can be defined by a radiation dose per treatment and a number of radiation treatments (or fractionation). Optionally, the method can further include administering radiation therapy to the subject at the radiation dose.

An example system for developing a radiation therapy treatment plan for a subject having a tumor is also described herein. The system can include a processor and a memory operably coupled to the processor. The memory can have computer-executable instructions stored thereon that, when executed by the processor, cause the processor to determine a radiosensitivity index of the tumor, derive a subject-specific variable based on the radiosensitivity index, and obtain a genomic adjusted radiation dose effect value for the tumor. The radiosensitivity index can be assigned from expression levels of signature genes of a cell in the tumor. The signature genes can include, but are not limited to, Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); and/or Interferon regulatory factor 1 (IRF1). Additionally, the genomic adjusted radiation dose effect value can be predictive of tumor recurrence in the subject after treatment. The memory can have further computer-executable instructions stored thereon that, when executed by the processor, cause the processor to determine a radiation dose based on the subject-specific variable and the genomic adjusted radiation dose effect value. The radiation dose can be defined by a radiation dose per treatment and a number of radiation treatments (or fractionation).

As described above, the radiation dose can be defined by the number of radiation treatments and the radiation dose per radiation treatment, e.g., the number of radiation treatments times the radiation dose per treatment. Optionally, determining a radiation dose can include determining the number of radiation treatments. Optionally, determining a radiation dose can include determining the radiation dose per treatment. Optionally, the radiation dose per treatment can be the standard clinical dose. For example, the radiation dose per treatment can be approximately 2 Gray ("Gy"). It should be understood that the radiation dose per treatment can be another dosage, e.g., more or less than 2 Gy.

Alternatively or additionally, the genomic adjusted radiation dose effect value for the tumor can optionally be a range of values predictive of tumor recurrence in the subject after treatment.

Alternatively or additionally, the genomic adjusted radiation dose effect value for the tumor can optionally be indicative of a low chance of tumor recurrence in the subject after treatment.

Alternatively or additionally, the genomic adjusted radiation dose effect value for the tumor can optionally be specific to a type of cancer. For example, the type of cancer can include, but is not limited to, breast, lung, prostate, glioblastoma, head and neck, pancreas, esophagus, or colorectal cancer. It should be understood that the type of cancer can be a type of cancer other than those listed herein.

Alternatively or additionally, the genomic adjusted radiation dose effect value can optionally be determined by analyzing the respective treatment plans and outcomes for a group of subjects (e.g., a plurality of subjects). The analysis can optionally be performed retrospectively. For example, a univariate or multivariate analysis of genomic dose effect values and outcomes for a group of subjects that have received radiation treatment can optionally be performed.

Alternatively or additionally, the subject-specific variable can optionally provide a measure of the tumor's ability to accumulate radiation damage.

Alternatively or additionally, the subject-specific variable can optionally be derived using a linear quadratic model for cell survival. The radiosensitivity index can be approximately equal to cell survival (e.g., cell survival at a radiation dose of 2 Gy).

It should be understood that the above-described subject matter may be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 5 is a table showing the results of the evaluation of six clinical cohorts of subjects.

FIG. 7A illustrates transforming physical radiation dose to genomic adjusted radiation dose (GARD). FIG. 7B represents the distribution of physical doses in the highest GARD level (top 10.6% of GARD scores). FIG. 7C represents the distribution of physical doses in the middle GARD level (30.41st-89.4th percentile of GARD scores). FIG. 7D represents the distribution of physical doses in the lowest GARD level (bottom 30.4th percentile). FIG. 7E represents data for disease sites treated with >70 Gy. FIG. 7F represents disease sites treated with 60 Gy. FIG. 7G represents disease sites treated with 45 Gy.

FIG. 8A illustrates transforming physical radiation dose to genomic adjusted radiation dose (GARD). FIG. 8B represents the distribution of physical doses in the highest GARD level. FIG. 8C represents the distribution of physical doses in the middle GARD level. FIG. 8D represents the distribution of physical doses in the lowest GARD level. FIG. 8E shows a weak but significant correlation between GARD and $BED_{2.88}$. FIG. 8F demonstrates that patients that achieve the GARD threshold dose level have an improved DMFS that is statistically significant. FIG. 8G shows that $BED_{2.88}$ does not predict for DMFS.

FIG. 9 is a table illustrating the multivariable analysis of GARD in the Erasmus Breast Cancer cohort.

FIG. 10A illustrates that GARD provides a paradigm to inform RT dose clinical decisions based on individual tumor genomics. FIG. 10B illustrates the probability of achieving the GARD threshold dose level (GARD>38.9) in an unselected population is shown as a function of physical dose. FIG. 10C illustrates the potential therapeutic benefit of RT dose escalation is estimated using the estimates of GARD-high/low sub-populations achieved at each physical dose of FIG. 10B and normalized to the effect at 50Gy.

DETAILED DESCRIPTION

Figure 1:
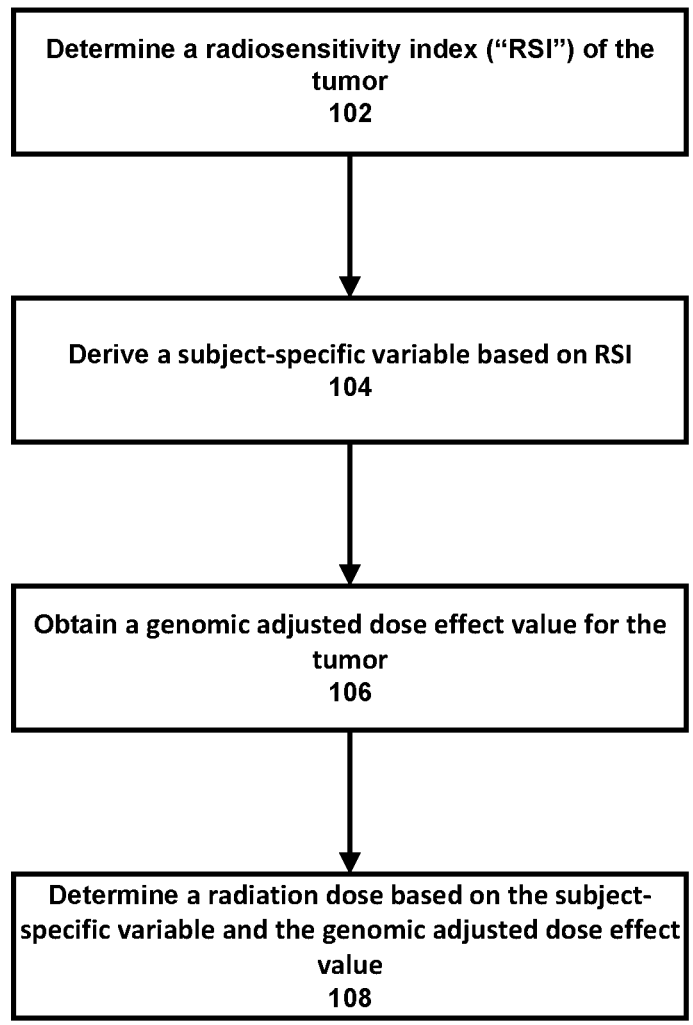
FIG. 1 is a flow diagram illustrating example operations for treating a subject having a tumor.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for treating a subject having a tumor, it will become evident to those skilled in the art that the implementations are not limited thereto.

The methods described herein can be used to treat, or develop a treatment plan for, any solid tumor in a subject. A solid tumor is an abnormal mass of hyperproliferative or neoplastic cells from a tissue other than blood, bone marrow, or the lymphatic system, which may be benign or cancerous. In general, the tumors treated by the methods described herein are cancerous. As used herein, the terms "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of solid cancerous growths, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. Examples of solid tumors are sarcomas, carcinomas, and lymphomas. Leukemias (cancers of the blood) generally do not form solid tumors.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some implementations, the disease is lung carcinoma, rectal carcinoma, colon carcinoma, esophageal carcinoma, prostate carcinoma, head and neck carcinoma, or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some implementations, the tumors treated by a method described herein are of epithelial cell origin. In some implementations, the tumors originate from lung, colon, rectal, esophageal, prostate, or head/neck tissues (e.g., originating from the upper aerodigestive tract, including the lip, oral cavity, nasal cavity, paranasal sinuses, pharynx, and larynx, e.g., squamous cell carcinomas originating from the mucosal lining (epithelium)). In some implementations, the tumors are metastatic, and originate from an epithelial tissue (and are thus epithelial in origin) but have spread to another tissue, e.g., epithelial-origin prostate cancer that has spread to the bones of the pelvis, spine and/or ribs, or lung carcinoma that has metastasized to the adrenal glands, liver, brain, or bones.

Referring now to FIG. 1, example operations 100 for treating a subject having a tumor are described. At 102, a radiosensitivity index ("RSI") of the tumor is determined. RSI can be assigned from expression levels of one or more signature genes of a cell or cells in the subject's tumor. This disclosure contemplates that RSI can be determined using a computing device, for example. One or more assays of cell(s) of the subject's tumor can be performed to determine gene expression levels. For example, any known technique for obtaining a sample comprising at least one living cell (preferably a plurality of cells), e.g., a cell from the subject's tumor (e.g., from a biopsy) can be used. Commonly used methods to obtain tumor cells include surgical (e.g., the use of tissue taken from the tumor after removal of all or part of the tumor) and needle biopsies. The samples should be treated in any way that preserves intact the gene expression levels of the living cells as much as possible, e.g., flash freezing or chemical fixation, e.g., formalin fixation. Additionally, any known technique can be used to extract material, e.g., protein or nucleic acid (e.g., mRNA) from the sample. For example, mechanical or enzymatic cell disruption can be used, followed by a solid phase method (e.g., using a column) or phenol-chloroform extraction, e.g., guanidinium thiocyanate-phenol-chloroform extraction of the RNA. A number of kits are commercially available for use in isolation of mRNA.

The signature genes can include, but are not limited to, Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); and/or Interferon regulatory factor 1 (IRF1). It should be understood that the signature genes can include one or more other genes not listed above, which are provided only as examples. For example, RSI can be assigned using a linear regression model of gene expression levels as described in U.S. Pat. No. 8,660,801 to Torres-Roca et al., issued Feb. 25, 2014, entitled "Gene signature for the prediction of radiation therapy response," the disclosure of which is incorporated by reference in its entirety herein. As described therein, RSI provides an indication of whether radiation therapy is likely to be effective in treating the subject's tumor. RSI has a value approximately between 0 and 1. Eschrich et al., Systems biology modeling of the radiosensitivity network: a biomarker discovery platform, Int. J. Radiat. Oncol. Biol. Phys. (2009). It should be understood that assigning RSI according to the linear regression model of gene expression levels described in U.S. Pat. No. 8,660,801 is provided only as an example and that other known techniques for assigning radiation sensitivity can optionally be used with the systems and methods described herein.

Example methods for determining RSI use a rank-based linear algorithm to assign an RSI to a cell, e.g., a living cell such as a tumor cell from a patient, a normal cell from a patient, or a cultured cell. In general, the methods are applicable to any mammal, particularly humans. The methods include determining expression levels of signature genes in a cell or cells of the tumor, and determining a RSI based on the expression levels. In some implementations, the methods include the use of two or more, e.g., three, four, five, six, seven, eight, nine, or all ten signature genes as shown in Table 1.

TABLE 1

| Gene Name |
| --- |
| Androgen receptor |
| c-Jun |
| STAT1 |
| PKC |
| RelA (p65) |
| c-Abl |
| SUMO-1 |
| PAK2 |

TABLE 1-continued

Gene Name

HDAC1
IRF1

Although the exemplary gene sequences set forth above are for the human genes, and thus are best suited for use in human cells, one of skill in the art could readily identify mammalian homologs using database searches (for known sequences) or routine molecular biological techniques (to identify additional sequences). In general, genes are considered homologs if they show at least 80%, e.g., 90%, 95%, or more, identity in conserved regions (e.g., biologically important regions).

A linear regression model useful in the methods described herein includes gene expression levels and coefficients, or weights, for combining expression levels. The coefficients can be calculated using a least-squares fit of the proposed model to a measure of cellular radiation sensitivity. One example described herein used the survival fraction at 2 Gy ("SF2") although other measures at other dose levels (e.g., SF8) can be considered with different coefficients being determined from each. The functional form of the algorithm is given below, wherein each of the $k_i$ coefficients will be determined by fitting expression levels to a particular RSI measure.

$$RSI = k_1 * AR + k_2 * c\text{-}jun + k_3 * STAT1 + k_4 * PKC + k_5 * RelA +$$
$$k_6 * cAbl + k_7 * SUMO1 + k_8 * PAK2 + k_9 * HDAC + k_{10} * IRF1$$

In some implementations, the methods include applying an algorithm to expression level data determined in a cell; e.g., a rank-based linear regression algorithm as described herein. In some implementations, the algorithm includes weighting coefficients for each of the genes.

At 104, a subject-specific variable can be derived based on RSI. This disclosure contemplates that the subject-specific variable can be derived using a computing device, for example. The subject-specific variable can optionally be derived using a linear quadratic model for cell survival. For example, RSI is a molecular estimate of the survival fraction at 2 Gy ("SF2"). RSI can therefore be substituted for Survival in the standard linear quadratic model for cell survival as shown in Eqn. (1) below.

$$RSI = e^{-\alpha d - \beta d[<]BEGINITAL m2}, \quad (1)$$

where $\alpha$ and $\beta$ are variables that provide measures of a tumor's ability to accumulate radiation damage, and d is the radiation dose (e.g., the radiation dose per treatment as used herein).

Using Eqn. (1), and assuming $\beta$ is a constant for standard fractionation and d is 2 Gy (e.g., the standard clinical dose), the subject-specific variable (e.g., a) can be derived after determining RSI (e.g., the RSI determined at 102). For example, $\beta$ is assumed to be constant and can be obtained using techniques known in the art, for example, as described in Lea D E. Actions of Radiation on Living Cells. Cambridge: University Press; 1946. It should be understood that RSI can be determined at other dose levels (e.g., SF8). In these cases, d would have a value more or less than 2 Gy in Eqn. (1). In other words, although the value of d is dependent on the RSI determination, the value of d is known. The derived subject-specific variable (e.g., $\alpha$) can then be used to determine the desired radiation dose as described below.

At 106, a genomic adjusted radiation dose effect value for the tumor is obtained. This disclosure contemplates that the genomic adjusted radiation dose effect value can be obtained using a computing device, for example. The genomic adjusted radiation dose effect value can be predictive of tumor recurrence in the subject after treatment. The genomic adjusted radiation dose effect value for the tumor can optionally be indicative of a low chance of tumor recurrence in the subject after treatment. Optionally, the genomic adjusted radiation dose effect value for the tumor can optionally be a range of values. As used herein, genomic adjusted radiation dose effect ("GARD") is a measure of effectiveness of radiation therapy. A higher GARD implies a higher predicted radiation therapy effect. A lower GARD implies a lower predicted radiation therapy effect. GARD is specific to a type of cancer, e.g., including, but not limited to, breast, lung, prostate, glioblastoma, head and neck, pancreas, esophagus, or colorectal cancer. In other words, GARD high/GARD low values (or range of values) are specific to a type of cancer, as well as the specific clinical indication. In some implementations, the GARD value for a particular type of cancer has been predetermined and is stored in memory of a computing device for later reference. In other implementations, the GARD value for a particular type of cancer is determined and then optionally stored in the memory of a computing device for later reference.

It should be understood that GARD high/GARD low values (or range of values) can be determined (e.g., calculated) by analyzing GARD and outcome for a group of subjects (e.g., a plurality of subjects) having the same type of cancer. GARD can optionally be determined by analyzing the respective treatment plans (e.g., dose per treatment, number of treatments/fractionation, etc.) for the group of subjects with known outcomes (e.g., distant metastasis-free survival ("DMFS"), overall survival ("OS"), etc.). The analysis can optionally be performed retrospectively. For example, a univariate or multivariate analysis can optionally be performed to obtain GARD high/GARD low values for the group of subjects. The analysis can reveal a particular GARD value (or range of values) that is predicted to achieve a positive outcome. In other words, the analysis can be used to determine a particular GARD value (or range of values) that reduces a subject's risk of tumor reoccurrence after radiation treatment. It should be understood that the particular GARD value (or range of values) can be used prospectively in the treatment of a subject.

Then, at 108, a radiation dose can be determined based on the subject-specific variable (e.g., $\alpha$) and the genomic adjusted radiation dose effect value. This disclosure contemplates that the radiation dose can be determined using a computing device, for example. The radiation dose can be determined by the radiation dose per treatment (e.g., 2 Gy) and the number of radiation treatments. For example, the radiation dose can be determined by the number of radiation treatments times the dose per radiation treatment. As described below, when the radiation dose per treatment is known (e.g., a standard dose of 2 Gy), the number of radiation treatments (or fractionation) can be determined or selected to achieve a particular GARD value for the subject, for example a high GARD value that likely reduces the subject's risk of tumor reoccurrence after radiation therapy. GARD is a subject-specific measure of the radiobiology parameter for dose effect shown in Eqn. (2) below.

$$GARD = nd(\alpha + \beta d), \quad (2)$$

where α and β are variables that provide measures of a tumor's ability to accumulate radiation damage, d is the radiation dose (e.g., the radiation dose per treatment as used herein), and n is the number of radiation treatments (or fractionation).

Eqn. (2) can be used to determine the number of radiation treatments. Specifically, the GARD value obtained at 106 is predictive of tumor recurrence in the subject after treatment, and optionally indicative of a low chance of tumor recurrence in the subject after treatment. Additionally, β is a constant for standard fractionation, d is 2 Gy (e.g., the standard clinical dose), and α (e.g., the subject-specific variable) is derived at 104. In other words, using Eqn. (2), the number of radiation treatments (or fractionation) for achieving a predicted outcome can be determined. In this way, the radiation treatment is personalized for the subject. Optionally, radiation therapy is administered to the subject at the radiation dose per treatment (e.g., 2 Gy) and/or the number of radiation treatments (e.g., n determined at 108).

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
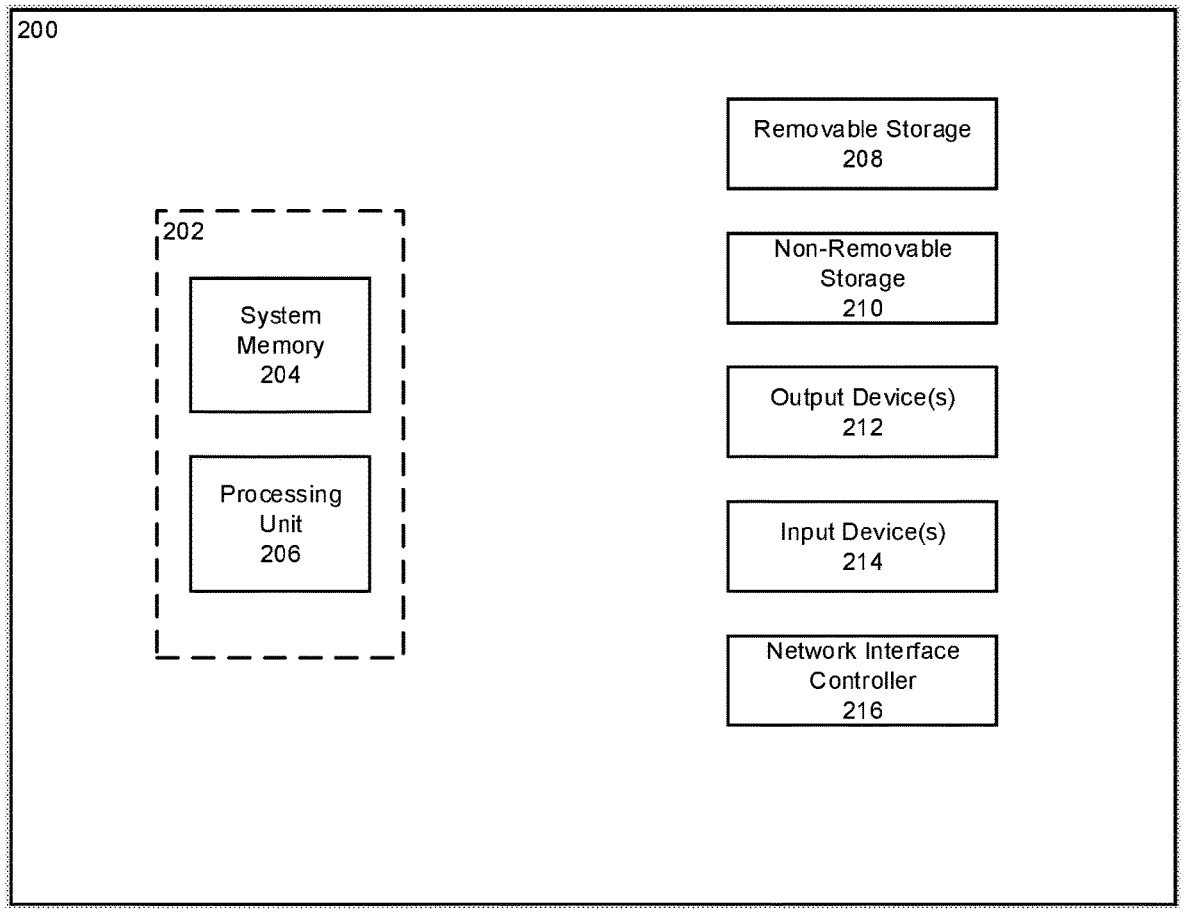
FIG. 2 is an example computing device.

When the logical operations described herein are implemented in software, the process may execute on any type of computing architecture or platform. For example, referring to FIG. 2, an example computing device upon which embodiments of the invention may be implemented is illustrated. The computing device 200 may include a bus or other communication mechanism for communicating information among various components of the computing device 200. In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Computer-readable media refers to any media that is capable of providing data that causes the computing device 200 (i.e., a machine) to operate in a particular fashion. Various computer-readable media may be utilized to provide instructions to the processing unit 206 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

Computing device 200 typically includes a variety of computer-readable media. Computer-readable media can be any available media that can be accessed by device 200 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 204, removable storage 208, and non-removable storage 210 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media may be part of computing device 200.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 3:
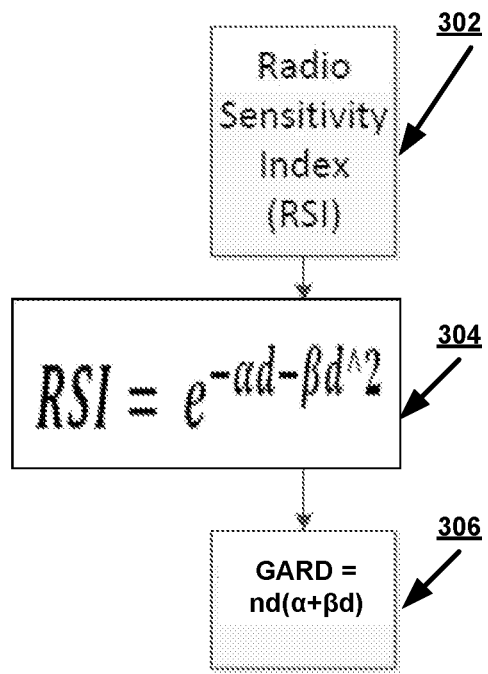
FIG. 3 is a flow diagram illustrating example operations for determining a personalized radiation dose using RSI.

Referring now to FIG. 3, a flow diagram illustrating example operations for determining a personalized radiation dose using RSI is shown. In FIG. 3, at 302, a subject-specific variable (e.g., α) is derived based on RSI, which is a molecular estimate of the survival fraction at 2 Gy. Using the subject-specific variable, at 304, the number of radiation treatments (e.g., n) to achieve a predetermined GARD, assuming the other values (e.g., dose per radiation treatment (d) and β) are known.

Figure 4:
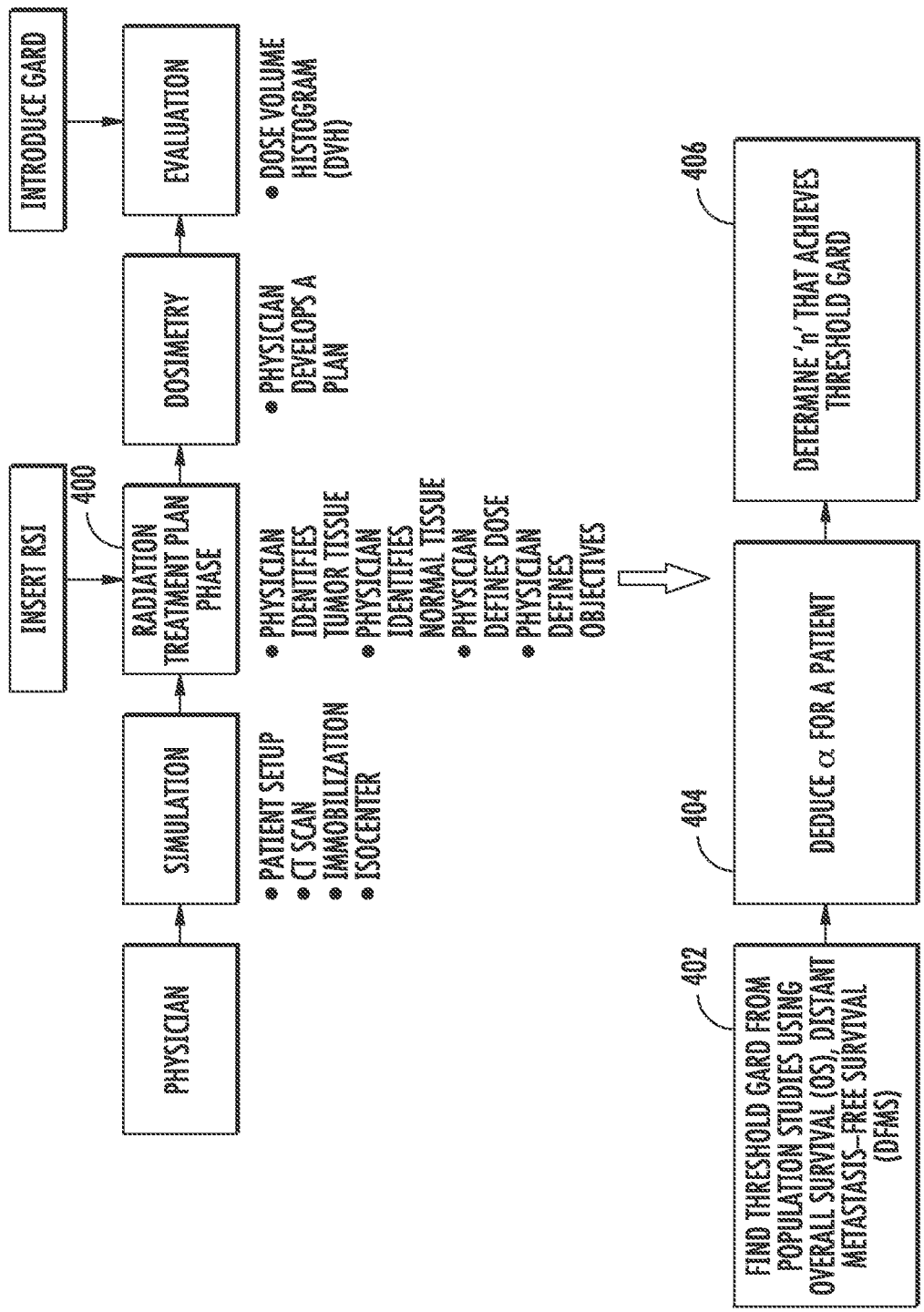
FIG. 4 is a flow diagram illustrating example operations for developing a personalized radiation treatment plan for a subject.

Referring now to FIG. 4, a flow diagram illustrating example operations for developing a personalized radiation treatment plan for a subject is shown. During the radiation treatment phase 400 of FIG. 4, at 402, a threshold GARD can optionally be determined by analyzing the respective treatment plans (e.g., dose per treatment, number of treatments/fractionation, etc.) for a group of subjects with known outcomes (e.g., distant metastasis-free survival ("DMFS"), overall survival ("OS"), etc.). At 404, a subject-specific variable (e.g., α) is derived based on RSI, which is a molecular estimate of the survival fraction at 2 Gy. Using the subject-specific variable, at 406, the number of radiation treatments (e.g., n) to achieve the threshold GARD, assuming the other values (e.g., dose per radiation treatment (d) and β) are known.

EXAMPLES

According to implementations described herein, RSI together with established radiobiological principles serve as the basis for precision medicine in radiation oncology. A genomic-adjusted radiation dose (GARD) can be derived by integrating a patient-specific RSI with physical RT dose and fractionation using the linear quadratic model. As described in detail below, it has been demonstrated, in a cohort of 8,271 patients across 20 different disease sites, that GARD exhibits wide heterogeneity both within and across solid tumor types in spite of uniform RT dose. Further, it has been shown that GARD is a superior predictor of clinical outcome compared to all variables including RSI in a cohort of breast cancer patients. Finally, it has been shown that GARD model identifies sub-populations that derive differential benefit from RT and can be utilized to individualize RT dose to optimize outcome.

GARD was evaluated in six independent clinical cohorts of subjects (e.g., patients) who received radiation therapy ("RT") (standard fractionation, FIG. 5). As shown in FIG. 5, the cohorts included three different breast cancer cohorts (e.g., n=77, 263, and 75, respectively, where n is the number of subjects), a lung cancer cohort (n=60), a glioblastoma cancer cohort (n=98), and a pancreatic cancer cohort (n=40). Gene expression was available from public sources or from the institutional bank of H. Lee Moffitt Cancer Center and Research Institute. RSI was calculated as described herein. Primary endpoints evaluated include recurrence free survival ("RFS"), distant metastasis-free survival ("DMFS"), local control ("LC") and overall survival ("OS"). GARD was compared to DMFS, LC or OS using univariate ("UVA") and multivariable ("MVA") Cox proportional hazard models.

A broad RSI distribution was observed for all cohorts, which leads to a large range of GARD values with clinically-relevant radiation doses. On UVA, GARD-low patients have worse outcome in five of the six cohorts that is statistically significant. The exception being the pancreatic cancer cohort. On MVA, GARD predicts outcome in all six cohorts. One possible reason why UVA and MVA yield different results as to whether GARD predicts outcome in the pancreatic cancer cohort is that a variable may not predict by itself because there is some other characteristic in the cohort of patients that opposes the effect of the variable. However, when the effect of all variables are taken into account, then the predictive value of the variable is revealed. Accordingly, MVA may provide the more important prediction. Additionally, it is estimated that a significant proportion of GARD-low patients in each cohort (8%-35%) would have met the threshold for the GARD-high group with customized and safe dose escalation.

Materials and Methods

Total Cancer Care (TCC) is a prospective IRB-approved tissue collection protocol active at H. Lee Moffitt Cancer Center and Research Institute and 17 other institutions since 2006[20]. Tumors from patients enrolled in TCC protocol were arrayed on Affymetrix Hu-RSTA-2a520709 (Affymetrix, Santa Clara, Calif.), which contains approximately 60,000 probesets representing 25,000 genes. Chips were normalized using iterative rank-order normalization (IRON)[21]. Dimensionality was reduced using partial-least squares (PLS). For this analysis, the normalized and de-batched expression values for 13,638 samples from 60 sites of origin and the ten RSI-genes were extracted from the TCC database. All metastatic, duplicate samples and disease sites with less than 25 samples were excluded. This resulted in 8,271 total samples from 20 sites of origin.

Erasmus Breast Cancer Cohort: The study was approved by the Medical Ethics Committee of the Erasmus Medical Center. Primary treatment was breast conserving therapy in 282 patients (lumpectomy+RT) and mastectomy alone for 62 patients. Detailed radiation records were available for 263 patients and these became the study population. Patients received whole breast RT with or without a boost to the tumor cavity, with total doses ranging from 45-74 Gy delivered 1.8-2 Gy per fraction. The distribution of clinical variables between the excluded patients and the final cohort were compared. Early metastasis was defined as a distant recurrence in the first 5 years following completion of primary treatment. Raw gene expression data was available in GEO (GSE2034, GSE5327).

Radiosensitivity Index (RSI)—RSI scores for the Erasmus dataset were previously generated[22]. Linear scaling was performed to avoid negative RSI values. Briefly, RSI was previously trained in 48 cancer cell lines to predict cellular radiosensitivity as determined by survival fraction at 2 Gy (SF2)[12]. Each of ten genes in the algorithm is ranked based on gene expression (highest expressed gene is ranked at 10 and lowest at 1), and RSI was calculated using the pre-determined algorithm below:

$$RSI=-0.0098009*AR+0.0128283*cJun+0.0254552*STAT1-0.0017589*PKC-0.0038171*RelA+0.1070213*cABL-0.0002509*SUMO1-0.0092431*PAK2-0.0204469*HDAC1-0.0441683*IRF1$$

This disclosure contemplates using other techniques for assigning radiation sensitivity with the systems and methods described herein, and therefore, this disclosure should not be limited to calculating RSI according to the algorithm provided above, which was used in the example study.

Biologically Effective Dose (BED)—BED was calculated assuming a constant $\alpha/\beta$ ratio of 2.88 for breast cancer as previously described[23,24].

Genomic Adjusted Radiation Dose (GARD)—GARD is derived using the linear quadratic (LQ) model, the individual RSI and the radiation dose and fractionation schedule for each patient.

Figure 6:
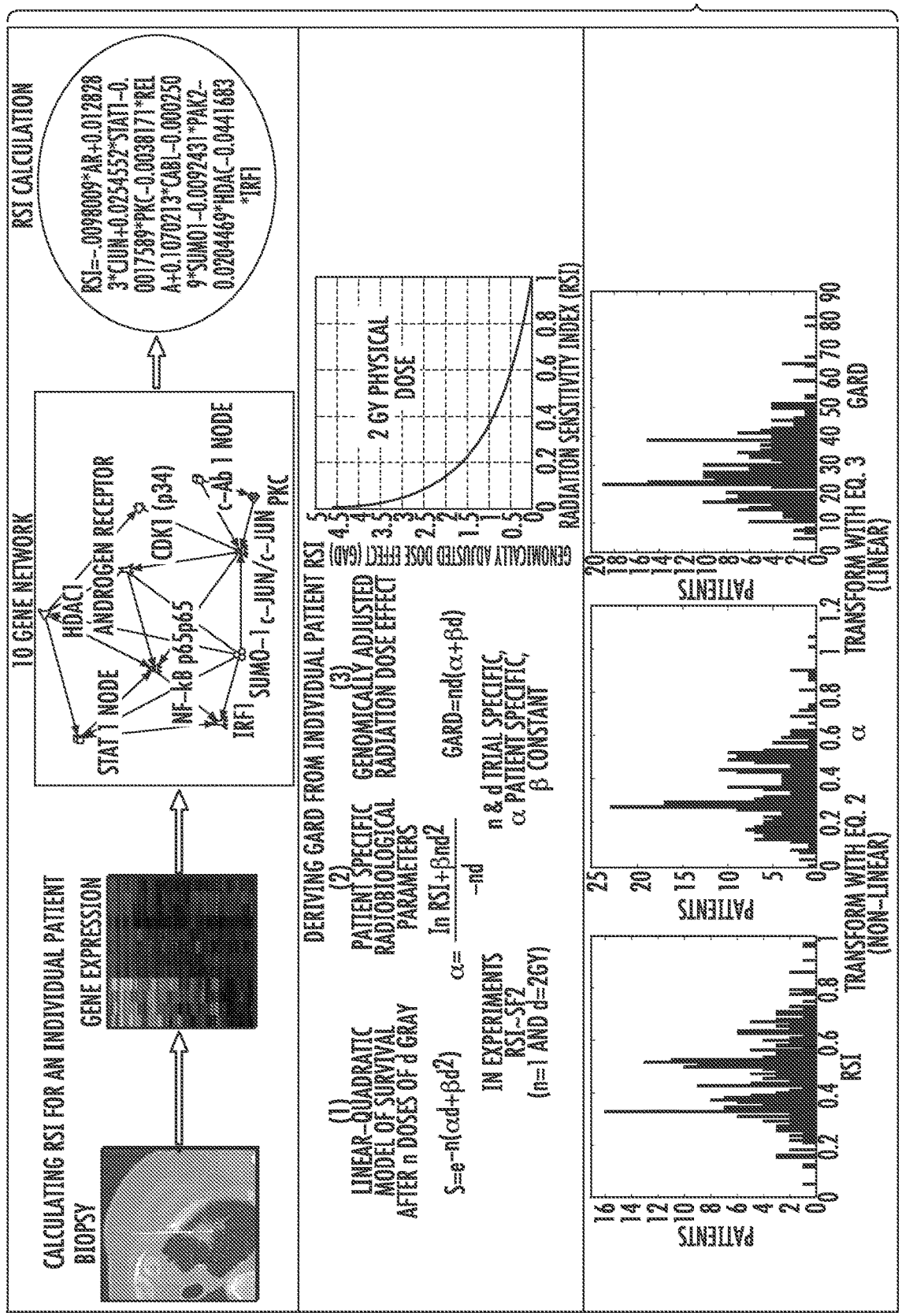
FIG. 6 is a diagram illustrating derivation of RSI from a tumor sample or biopsy (top panel) and derivation of GARD from RSI (middle panel). In the bottom panel, the distribution of RSI, cc, and GARD are shown for a cohort of 263 patients in the Erasmus Breast Cancer cohort.

Referring now to FIG. 6, a diagram illustrating derivation of RSI from a tumor sample or biopsy (top panel) and derivation of GARD from RSI (middle panel) is shown. Gene expression is determined for 10 specific genes, and a rank-based linear algorithm (e.g., the linear quadratic model shown by Eqn. 1 in FIG. 6) is utilized to calculate RSI. For example, RSI is substituted for S in the linear quadratic model of Eqn. 1 of FIG. 6, and a patient specific $\alpha$ is calculated assuming a $\beta$ (0.05/Gy$^2$), n=1 and d=2Gy as shown by Eqn. 2 of FIG. 6. GARD is then calculated based on Eqn. 3 of FIG. 6, using the patient-specific cc and the RT dose and fractionation received by each individual. The curve in the middle panel shows the non-linear relationship between RSI and GARD calculated for a single 2 Gy dose of RT. In the bottom panel, the distribution of RSI, $\alpha$ and GARD are shown for a cohort of 263 patients in the Erasmus Breast Cancer Cohort.

As shown by Eqn. 1 of FIG. 6, the LQ model in its simplest form is represented by:

$$S=e^{-nd(\alpha+\beta d)}, \quad (3)$$

where n is the number of fractions of radiation, d is the dose per fraction and $\alpha$ and $\beta$ represent the linear and quadratic radiosensitivity parameters, respectively.

Since RSI is a molecular estimate of SF2 in cell lines[12], a patient-specific $\alpha$ is derived by substituting RSI for Survival (S) in equation (3), where dose (d) is 2Gy, n=1 and $\beta$ is a constant (0.05/Gy$^2$)[25]. GARD is calculated using the classic equation for biologic effect shown by equation (2) above (i.e., E=nd($\alpha$+$\beta$d)), the patient-specific $\alpha$ and the radiation dose and fractionation received by each patient.

Statistical analyses—For the TCC analysis, differences in median GARD between disease sites were assessed using the Fisher Exact test. For the Erasmus dataset analysis, Distant Metastasis-Free Survival (DMFS) was estimated using the Kaplan-Meier method and the log-rank test was used to identify differences by GARD, dichotomized at the 75$^{th}$ percentile. This cut-point was pre-determined based on prior RSI analyses[22]. The association between DMFS with GARD grouping was assessed with multivariable Cox proportional hazards regression, adjusting for potential confounders and using a backward elimination model with a significant level-to-stay of 0.10. When comparing socio-demographic and clinico-pathological characteristics between the final Erasmus cohort and excluded patients, Fisher's Exact test was used to compare categorical variables including RSI, and Wilcoxon rank sum test for continuous variables. All analyses were conducted with SAS (version 9.3) of SAS Institute Inc. of Cary, N.C. and tests were two-sided with a significance level of 0.05.

The predicted benefit of RT dose escalation by the GARD-based model was calculated to be:

$$\frac{a*HR+(1-a)*1}{b*HR+(1-b)*1},$$

where a and b are the estimated percentage of patients that achieve the highest GARD dose level at physical RT dose range of 45-75 Gy. The HR (DM) for GARD-high patients was derived from the multivariable analysis of the Erasmus cohort (HR=2.11 or 0.47).

Results

Figure 7E:
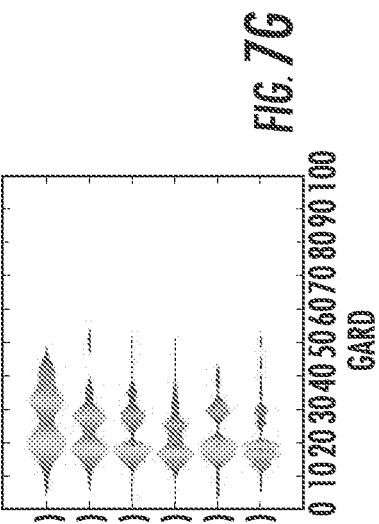
FIGS. 7A-7G illustrate a framework for genomic RT dose with reference to the TCC protocol described herein.
Figure 7F:
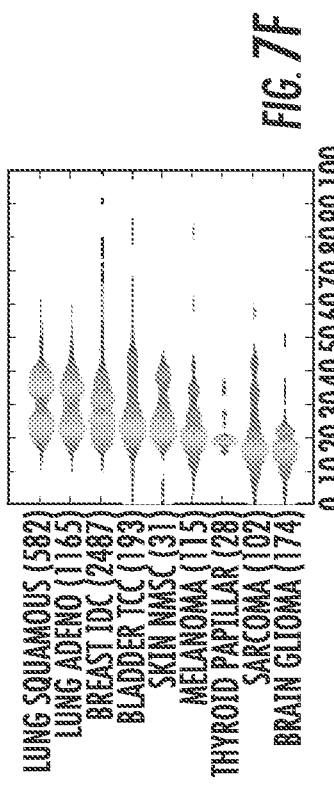
Figure 7F:
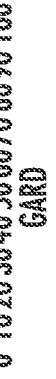
Figure 7G:
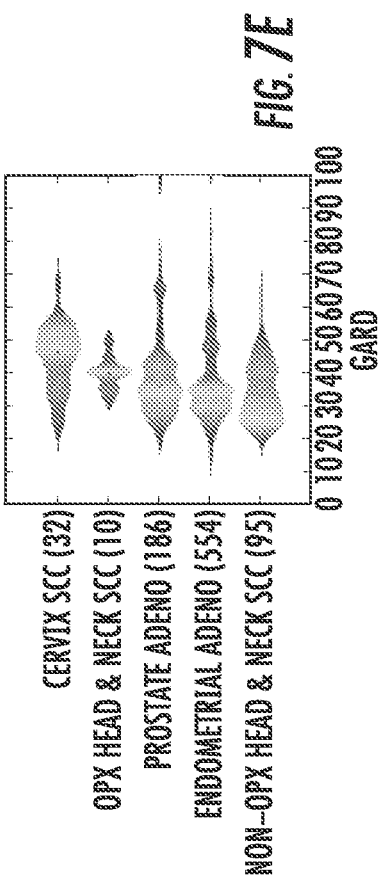
Figure 7B:
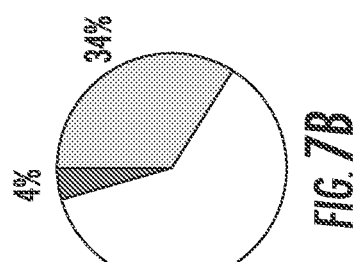
Figure 7C:
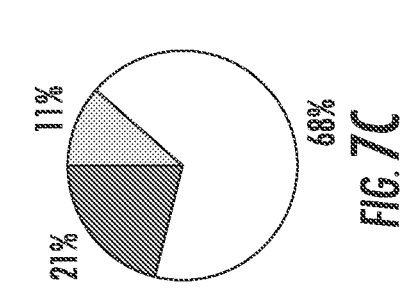
Figure 7D:
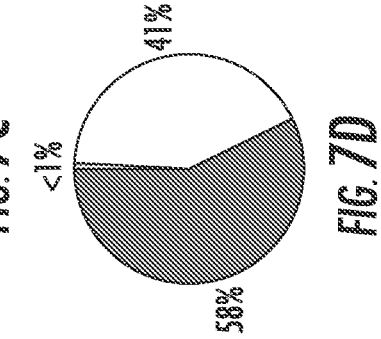
Figure 7A:
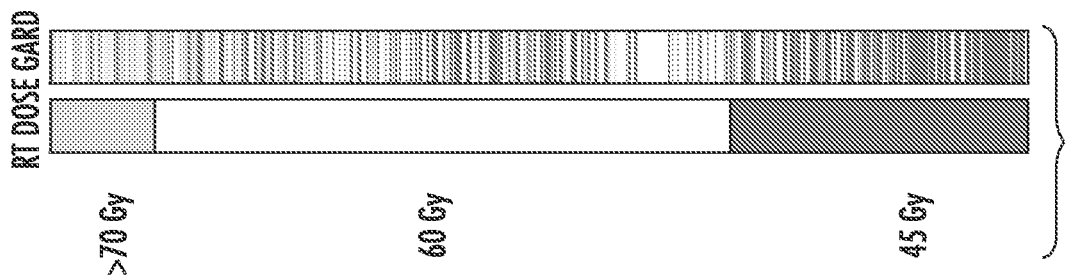

FIGS. 7A-7G illustrate a framework for genomic RT dose with reference to the TCC protocol described herein. GARD was calculated for 8,271 patients across 20 disease sites in TCC. FIG. 7A illustrates transforming physical radiation dose to genomic adjusted radiation dose (GARD). Standard RT doses for sub-clinical (45 Gy, black), microscopic (60 Gy, white) and macroscopic (>70 Gy, gray) disease are represented as discrete uniform blocks with the size of each block proportional to the number of patients in each group in TCC (30.4% for 45 Gy (black), 59% for 60 Gy (white) and 10.6% for >70 Gy (gray)). GARD values for each individual patient in the TCC cohort are presented ranked from the highest to lowest value. Each line in the GARD prism represents an individual patient and is colored based on the physical dose used to calculate GARD. These data demonstrate that significant heterogeneity in GARD results from uniform, one-size-fits all RT dose. In FIGS. 7B-7D, three GARD levels (low 0-30.4th percentile, middle 30.41th-89.4th percentile, and high 89.41-100 percentile) are defined to correspond to the same proportion of patients represented for each RT dose. Pie charts are shown demonstrating the proportion of patients at each physical dose level (45 Gy, black, 60 Gy, white and (>70 Gy, gray) in each GARD level. All physical doses are represented in each of the GARD levels. FIG. 7B represents the distribution of physical doses in the highest GARD level (top 10.6% of GARD scores), FIG. 7C represents the distribution of physical doses in the middle GARD level (30.41st-89.4th percentile of GARD scores), and FIG. 7D represents the distribution of physical doses in the lowest GARD level (bottom 30.4th percentile). FIG. 7E-7G present the GARD distribution for each disease site within each RT dose level ted. FIG. 7E represents data for disease sites treated with >70 Gy, FIG. 7F represents disease sites treated with 60 Gy, and FIG. 7G represents disease sites treated with 45 Gy.

Referring now to FIGS. 7A-7G, GARD, which is a clinical parameter that integrates a genomic patient-specific measure of tumor radiosensitivity with physical RT dose, is introduced. GARD was calculated for 8,271 patients using the RT dose and fractionation protocol that is standard for each of the 20 disease sites in the cohort and ranked GARD values from highest to lowest. A higher GARD value predicts a higher RT effect. Three RT dose levels that are commonly utilized for sub-clinical (45 Gy), microscopic (60 Gy) and macroscopic disease (≥70 Gy) were used, as shown in FIG. 7A. Each RT dose level (45 Gy, 60 Gy≥70 Gy) was represented by 30.4%, 59% and 10.6% of the patients in the TCC cohort. To facilitate the analysis, three GARD dose levels were defined to correspond to the same proportion of patients within each RT dose cohort (low 0-30.4$^{th}$ percentile, middle 30.41$^{th}$-89.4$^{th}$ percentile, and high 89.41$^{st}$-100$^{th}$ percentile). As shown in FIGS. 7A-7D, GARD reveals significant heterogeneity that results from uniform RT dose across the TCC cohort. For example, although most of the patients that are normally treated with 45 Gy are expected towards the bottom of the GARD scale (58% of patients in the lowest GARD level as shown in FIG. 7D), a significant group is present near the middle of the scale (21% of patients in the middle GARD level as shown in FIG. 7C). The same observation is seen with patients treated with doses above 70 Gy. The majority of these patients are at the very top of the distribution for GARD (34% of patients in the highest GARD level as shown in FIG. 7B), but a significant proportion of patients are found in the middle GARD level (11% of patients in the middle GARD level as shown in FIG. 7C). Finally, the largest patient subset (60 Gy) was distributed throughout the scale with patients in all three GARD dose levels as shown in FIGS. 7B-7D. Thus, a higher dose does not always result in a higher dose effect as predicted by GARD.

Next, each of the dose cohorts was evaluated individually for the TCC protocol as shown in FIG. 7E-7G. Cervical cancer and oropharynx head and neck cancer had the highest GARD, consistent with the high radiocurability of these tumors. Importantly, GARD demonstrates that RT to 70 Gy has a higher predicted effect in oropharynx when compared to non-oropharynx head and neck cancer (Median GARD 46.32 vs. 32.56, p=0.04), also consistent with known clinical data. In the group of disease sites normally treated to 60 Gy, GARD identifies glioma (median GARD=16.55) and sarcoma (median GARD=17.94) as the two disease sites with the least effect from uniform RT when compared to all other disease sites at this dose level (p<0.0001). Furthermore, GARD also estimates that RT effect at 60 Gy is larger in non-melanoma skin cancer when compared with melanoma (median GARD, non-melanoma vs. non-melanoma 25.80 vs. 21.17, p=0.01). Finally at the 45 Gy dose level, GARD identifies a higher RT dose effect for esophageal cancer, when compared with rectal cancer (p=0.0003). This is consistent with data for pre-operative chemoradiation where the pathological complete response to 5-FU-based chemoradiation is higher in esophageal when compared with rectal cancer. In addition, GARD identifies a higher predicted RT effect for stomach cancer when compared with pancreas (p=0.002). Both of these disease sites are commonly treated with post-operative RT, with evidence for a higher RT impact in stomach.

Figure 8E:
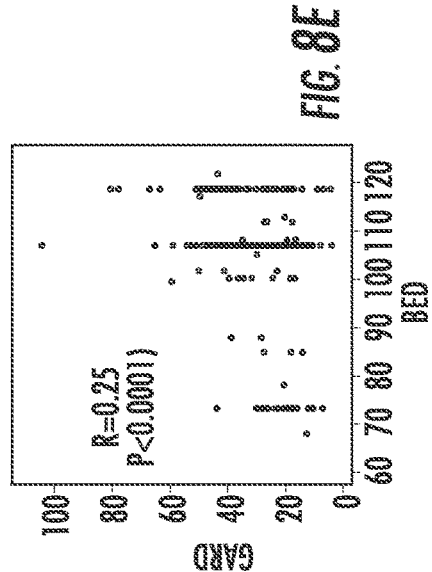
FIGS. 8A-8G illustrate a framework for genomic RT dose with reference to the Erasmus Breast Cancer cohort described herein.
Figure 8F:
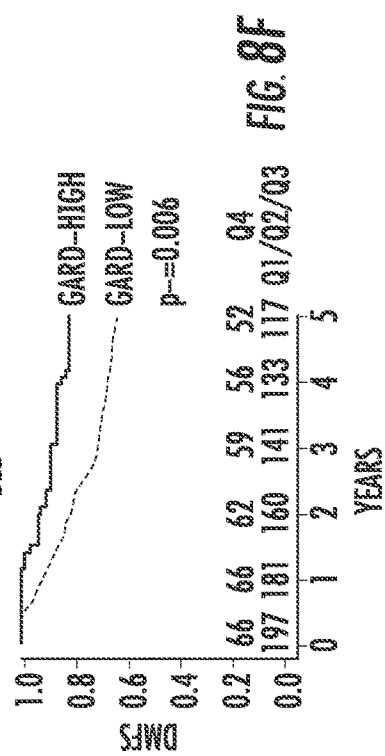
Figure 8G:
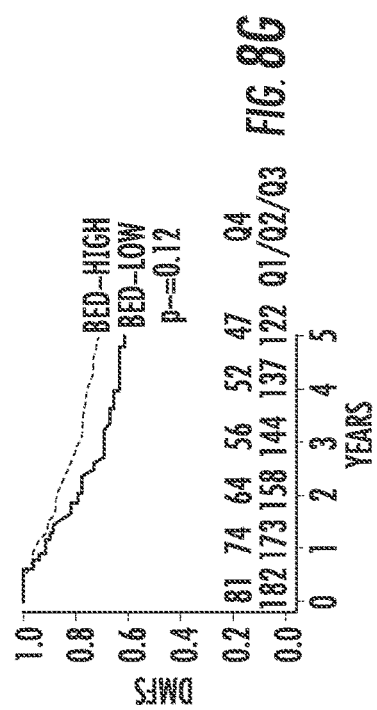
Figure 8B:
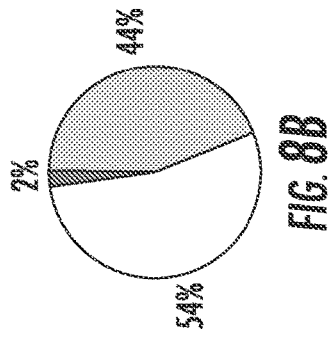
Figure 8C:
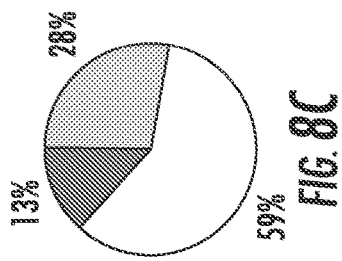
Figure 8D:
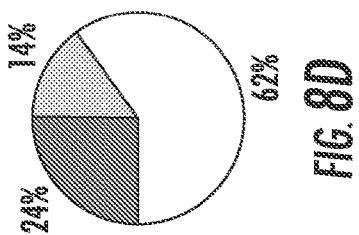
Figure 8A:
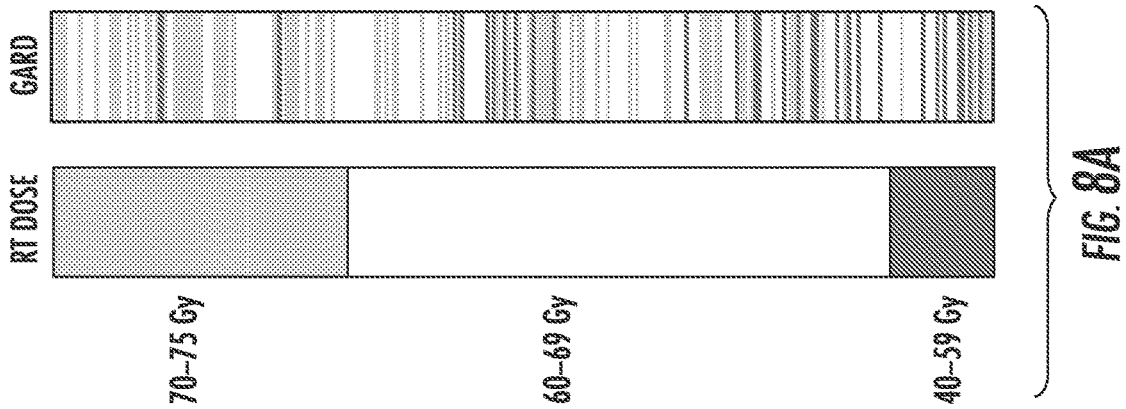

To further evaluate GARD, it was tested for the Erasmus Breast Cancer Cohort where detailed information on RT dose delivered, genomic information and mature clinical outcome was available (Erasmus dataset). FIGS. 8A-8G illustrate a framework for genomic RT dose with reference to the Erasmus Breast Cancer cohort described herein. GARD predicts for Distant Metastasis-Free Survival (DMFS) in Breast Cancer. GARD and BED$_{2.88}$ were generated for 263 lymph node negative patients treated with surgery and post-operative RT to the whole breast with or without a tumor cavity boost. FIG. 8A illustrates transforming physical radiation dose to genomic adjusted radiation dose (GARD). RT doses received by each patient in the cohort ranged from 40 Gy to 75 Gy. These were divided in three RT dose levels: low (black, 40-59 Gy, about 10% of patients), intermediate (white, 60-69 Gy, about 65% of patients) and high (gray, 70-75 Gy, about 25% of patients) and are represented as discrete uniform blocks with the size of each block proportional to the number of patients in each group. GARD values for each individual patient in the cohort are presented ranked from the highest to lowest value. Each line in the GARD prism represents an individual patient and is colored based on the physical dose received by the patient. In FIGS. 8B-8D, three GARD levels to correspond to the same proportion of patients represented for each RT dose range are defined. Pie charts are shown demonstrating the proportion of patients from each physical dose level in each GARD level. All physical doses are represented in each of the GARD levels. FIG. 8B represents the distribution of physical doses in the highest GARD level, FIG. 8C represents the distribution of physical doses in the middle GARD level, and FIG. 8D represents the distribution of physical doses in the lowest GARD level. FIG. 8E shows a weak but significant correlation between GARD and BED$_{2.88}$. FIG. 8F demonstrates that patients that achieve the GARD threshold dose level have an improved DMFS that is statistically significant. FIG. 8G shows that BED$_{2.88}$ does not predict for DMFS.

As shown in FIG. 8A, this cohort was treated with a wide range of RT total dose (40-75 Gy). Similarly to observations for the TCC protocol, transformation to genomic dose (GARD) revealed significant heterogeneity achieved within this RT dose range as shown in FIG. 8A with all RT dose cohorts represented throughout the GARD spectrum as shown in FIGS. 8B-8D. To serve as a control, BED$_{2.88}$ was also generated, assuming a uniform parameter for radiosensitivity α/β=2.88). As shown in FIG. 8E, there was a weak but significant correlation between GARD and BED$_{2.88}$ (R=0.25, p<0.0001). Patients that achieved the GARD-threshold dose level for this cohort (GARD≥38.9) have an improved distant-metastases free survival (DMFS) (FIG. 8F, HR=2.31 (1.25, 4.25), p=0.006). In contrast, BED$_{2.88}$ did not predict for DMFS in univariable analysis (FIG. 8G, p=0.12). On multivariable analyses, GARD is an independent predictor of outcome (e.g., Table of FIG. 9, HR=2.11 (1.13, 3.94), p=0.01).

Referring now to FIG. 9, a table illustrating the multivariable analysis of GARD in the Erasmus Breast Cancer cohort is shown. GARD is treated as a dichotomous variable with a pre-specified cut-point at the 75$^{th}$ percentile. GARD is an independent variable that predicts clinical outcome in breast cancer.

Finally, to compare GARD to RSI, backward elimination in the multivariable model fitting with candidate variables (ER/PR status, T stage, age, GARD, BED$_{2.88}$ and RSI) was used. GARD (p=0.008) was the only remaining significant variable in the model.

Figures 10A, 10B, 10C:
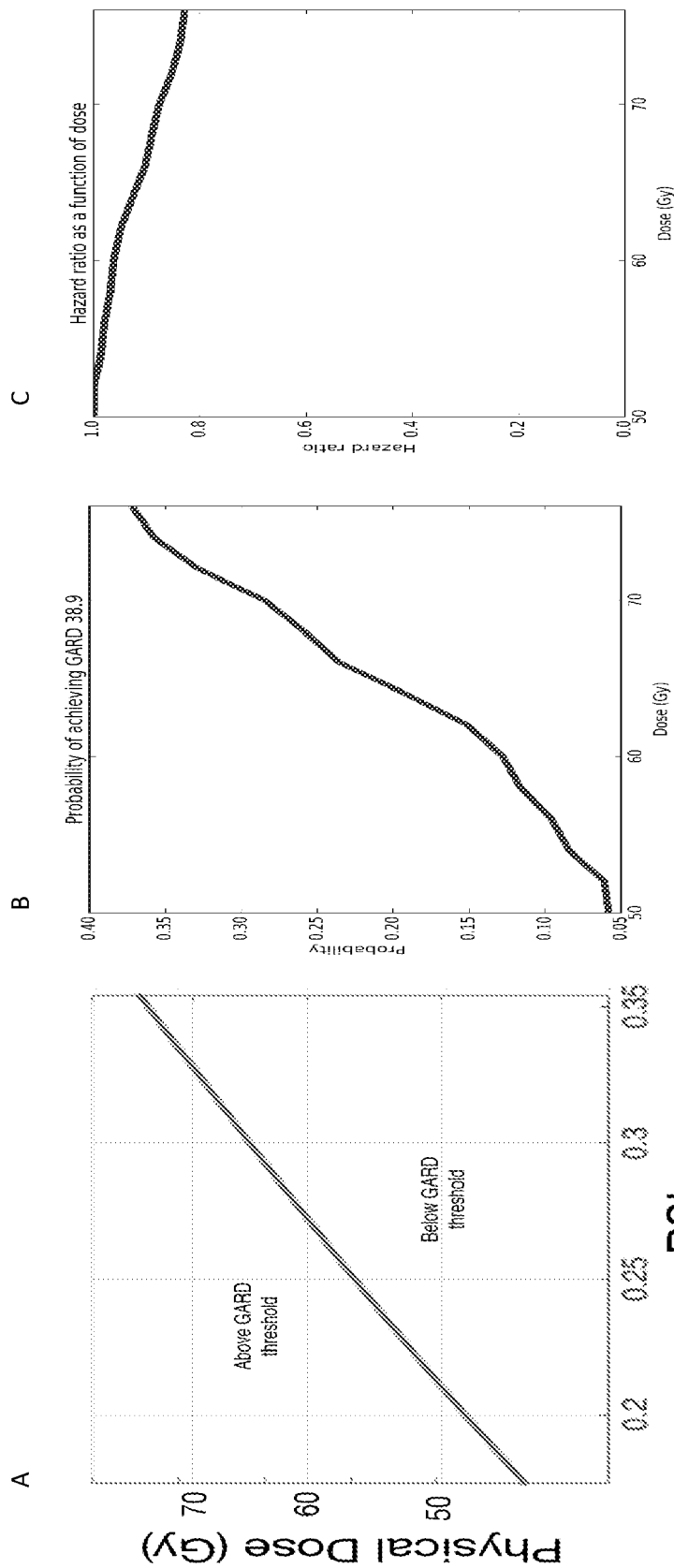
FIGS. 10A-10C are graphs illustrating genomically-informed RT.

Referring now to FIGS. 10A-10C, graphs illustrating genomically-informed RT. FIG. 10A illustrates that GARD provides a paradigm to inform RT dose clinical decisions based on individual tumor genomics. Physical dose is individualized in patients that are genomically-identifiable based on RSI and adjusted until a pre-determined GARD threshold value is achieved. The physical dose required to meet the GARD threshold dose level (GARD>38.9) is shown in FIG. 10A. As an example, a patient with an RSI value of 0.21 would require a dose of 50Gy to meet the threshold as shown in FIG. 10A. In contrast, an RSI value of 0.27 would require a dose of 60 Gy to achieve the same threshold as shown in FIG. 10A. It should be noted that this curve is based on the RT benefit calculated for DM (not local control). FIG. 10B illustrates the probability of achieving the GARD threshold dose level (GARD>38.9) in an unselected population is shown as a function of physical dose. The proportion of GARD-high patients increases from 5% to 36% in the dose range from 50 to 76 Gy. FIG. 10C illustrates the potential therapeutic benefit of RT dose escalation is estimated using the estimates of GARD-high/low sub-populations achieved at each physical dose of FIG. 10B and normalized to the effect at 50Gy. The GARD-based model predicts that a modest improvement in DMFS is maximized in a genomically-identifiable population.

A GARD-based platform to inform RT dose can provide the ability to individualize RT dose based on tumor genomics. RT dose can be individualized for genomically-identifiable patients, to achieve a predetermined GARD threshold value associated with best clinical outcome. FIGS. 10A-10C illustrates this concept where dose is adjusted to account for tumor radiosensitivity. A patient subset (RSI=0.18-0.35) is identified that achieves the GARD threshold receiving doses from 45-75 Gy as shown in FIGS. 10A and 10B. This subset represents 25% of breast cancer patients.

Next, the distribution of GARD-high/low sub-populations at each dose level (e.g., as shown in FIG. 10B) was used to estimate the potential benefit of genomically-informed RT dose. As shown in FIG. 10C, it is estimated that RT dose escalation results in an overall slight improvement in DMFS. However, these improvements would not be noticed in an unselected randomized trial. For example, the model estimates that dose escalation from 50 to 66 Gy would result in a small decrease in DMFS (HR=0.92). A trial with 80% power to detect this difference without genomic guidance would require 14,489 patients. In contrast, a GARD-directed trial targeting patients with the most potential for benefit would require 230 patients.

EORTC 22881-10882 randomized 5,318 patients to postoperative whole breast RT (50 Gy) with or without a 16 Gy boost[26,27]. Dose escalation resulted in a decrease in local recurrence risk (HR=0.59, 10-yr follow-up, HR=0.65, 17.2-years median follow-up) and no difference in DM at 20 years (HR 1.06, 0.92-1.24, p=0.29). The estimated DMFS benefit for dose escalation calculated by GARD (HR=0.92) is in the same range as these prospective results. Further, the estimated HR for DMFS is one-fourth the observed benefit for local recurrence (HR=0.65), consistent with the 4:1 relationship between local recurrence and breast cancer death observed in the EBCTCG meta-analysis[28]. These data demonstrate that GARD can be utilized to design genomically-guided clinical trials in radiation oncology.

DISCUSSION

A feasible approach to precision medicine in radiation oncology is described herein. GARD is a clinical parameter for genomic radiation dosing which allows the individualization of RT dose to match tumor radiosensitivity and provides a framework to design genomically-guided clinical trials in radiation oncology.

The clinical validity of GARD is supported by several lines of evidence. First, GARD is based on RSI and the linear quadratic model, both of which have extensive clinical validation. RSI has been validated as a predictor of outcome in multiple datasets of RT-treated patients, and the LQ model has served as the basis for dose and fractionation in clinical radiation oncology. Second, it was demonstrated that significant biological heterogeneity results from uniform one-size-fits all RT dose consistent with the clinical heterogeneity of RT benefit seen in the clinic. For example, glioma and sarcoma had the lowest GARD median value for all disease sites. In addition, GARD predicts higher RT impact in oropharynx HNC when compared with non-oropharynx, esophageal cancer when compared with rectal cancer, non-melanoma skin cancer when compared with melanoma and gastric cancer when compared with pancreatic cancer. All of these observations are consistent with results from clinical studies.

Third, the clinically utility of GARD was tested in a cohort of 263 breast cancer patients treated with surgery and RT. This cohort is ideal to test a radiation-related predictor since none of the patients received chemotherapy and/or hormonal therapy, thus limiting confounding factors. In addition, there was significant heterogeneity in the radiation doses delivered to the tumor cavity. The analyses show that GARD is an independent predictor of RT-specific outcome, outperforms both RSI and $BED_{2.88}$, and is, critically, clinically actionable through changes in RT dose. Furthermore, GARD was an independent predictor of clinical outcome in four additional independent cohorts including breast, GBM, lung and pancreas cancer patients.

The techniques described herein have several important implications. First, integration of classical radiobiology and genomics demonstrates that it is possible to identify genomically-distinct populations that derive differential benefit from RT. Further, a method by which to customize radiation dose to match the radiosensitivity of an individual patient has been provided. A framework to design genomically-stratified, RT-based trials using specifically defined genomic subpopulations has been provided. This brings radiation oncology in line with modern trial design for targeted agents, and, like the discovery of imatinib allowed for the age of targeted therapy[29], this heralds a new era of genomically-dosed RT. As shown herein, genomic-based clinical trial design can dramatically improve the efficiency of the clinical trials in radiation oncology. It can lead to a reduction in both the number of patients required to test a hypothesis and the time to complete the trial, both of which should lead to significant cost-savings. Finally, this model is RT-focused rather than disease-site focused. It has been demonstrated that wide heterogeneity in radiosensitivity across tumor types, and both RSI and GARD have been shown to predict for clinical outcome in multiple disease-sites. Thus, this could provide a rationale, and indeed a roadmap, to genomically guided RT-dose optimization in all cancers.

There is clinical opportunity for patient-specific dose optimization in breast cancer. RT doses have been empirically optimized leading to excellent local control rates and toxicity for breast cancer, although there are molecular sub-populations with higher risks for local recurrence following standard doses (i.e. TN-radioresistant)[17,30-32,33,34]. The framework described herein accepts all prior dose optimization and provides a way to move forward. Genomic subpopulations that derive differential benefit from RT (RSI) can be identified. There are modest clinical differences between patient subsets that are at least partly driven by RT dose effect (GARD). Since these differences only appear in specific subpopulations, they are not readily apparent in unselected clinical trials. Third, GARD-based RT dosing provides an approach to determine the required physical dose range to achieve the GARD threshold. Importantly, the dose ranges proposed for a significant proportion of patients (25%) can be delivered while respecting normal tissue constraints. Finally, this approach focuses on distant metastasis (DM) not local control (LC) as the clinical endpoint.

Solid clinical evidence from the Oxford meta-analysis now demonstrate unequivocally that RT decreases the risk of death presumably by decreasing the risk of DM[28]. Thus, there are still unrealized clinical gains in breast cancer that may result from understanding the impact of RT on the development of DM.

Several assumptions were made to complete the analyses described herein. Specifically, it was assumed that the recurrence risks and RSI distribution in the Erasmus cohort is similar to a normal lymph node negative breast cancer population. This is strengthened by the observation that the RSI distribution between Erasmus and TCC are similar. It was also assumed that the quadratic component of radiation response, $\beta$, is constant. As there has been no attempt to model different ranges of fractional (daily) dose, this assumption should not qualitatively affect the conclusions. Finally, while RSI was used in the analyses, the calculation of GARD can use any measure of radiosensitivity and/or be expanded to include other biological parameters involved in radiation response including hypoxia, DNA repair, proliferation and the immune system.

In conclusion, a central requirement for precision medicine in radiation oncology is the ability to inform radiation dose parameters to match individual tumor biology, thus delivering the right radiation dose for the right patient. The genomic adjusted radiation dose (GARD) described herein provides the ability to genomically-inform radiation dose and is also a safe and feasible approach to precision radiation oncology.

REFERENCES

1. Barnett G C, West C M, Dunning A M, et al. Normal tissue reactions to radiotherapy: towards tailoring treatment dose by genotype. Nat Rev Cancer 2009; 9:134-42.
2. Brown J M, Adler J R, Jr. Is Equipment Development Stifling Innovation in Radiation Oncology? Int J Radiat Oncol Biol Phys 2015; 92:713-4.
3. Roper N, Stensland K D, Hendricks R, Galsky M D. The landscape of precision cancer medicine clinical trials in the United States. Cancer Treat Rev 2015; 41:385-90.
4. Paik S, Shak S, Tang G, et al. A multigene assay to predict recurrence of tamoxifen-treated, node-negative breast cancer. N Engl J Med 2004; 351:2817-26.
5. van de Vijver M J, He Y D, van't Veer U, et al. A gene-expression signature as a predictor of survival in breast cancer. N Engl J Med 2002; 347:1999-2009.
6. Torres-Roca J F. A molecular assay of tumor radiosensitivity: a roadmap towards biology-based personalized radiation therapy. Per Med 2012; 9:547-57.
7. Mendelsohn J, Tursz T, Schilsky R L, Lazar V. WIN Consortium—challenges and advances. Nat Rev Clin Oncol 2011; 8:133-4.
8. Tursz T, Andre F, Lazar V, Lacroix L, Soria J C. Implications of personalized medicine—perspective from a cancer center. Nat Rev Clin Oncol 2011; 8:177-83.
9. Dalton W S, Friend S H. Cancer biomarkers—an invitation to the table. Science 2006; 312:1165-8.
10. Ahmed K A, Fulp W J, Berglund A E, et al. Differences Between Colon Cancer Primaries and Metastases Using a Molecular Assay for Tumor Radiation Sensitivity Suggest Implications for Potential Oligometastatic SBRT Patient Selection. Int J Radiat Oncol Biol Phys 2015.
11. Eschrich S, Fulp W J, Pawitan Y, et al. Validation of a Radiosensitivity Molecular Signature in Breast Cancer. Clin Cancer Res 2012.
12. Eschrich S, Zhang H, Zhao H, et al. Systems biology modeling of the radiation sensitivity network: a biomarker discovery platform. Int J Radiat Oncol Biol Phys 2009; 75:497-505.
13. Eschrich S A, Pramana J, Zhang H, et al. A gene expression model of intrinsic tumor radiosensitivity: prediction of response and prognosis after chemoradiation. Int J Radiat Oncol Biol Phys 2009; 75:489-96.
14. Strom T, Hoffe S E, Fulp W, et al. Radiosensitivity index predicts for survival with adjuvant radiation in resectable pancreatic cancer. Radiother Oncol 2015.
15. Torres-Roca J F, Eschrich S, Zhao H, et al. Prediction of Radiation Sensitivity Using a Gene Expression Classifier. Cancer Res 2005; 65:7169-76.
16. Torres Roca J F, Erho N, Vergara I, et al. A Molecular Signature of Radiosensitivity (RSI) is an RT-specific Biomarker in Prostate Cancer. ASTRO; 2014; San Francisco: International Journal of Radiation Oncology Biology Physics. p. S157.
17. Torres-Roca J F, Fulp W, Naghavi A O, et al. Integrating a Molecular Signature of Intrinsic Radiosensitivity into the Classification of Breast Cancer. Int J Radiat Oncol Biol Phys 2015:in press.
18. Ahmed K A, Eschrich S, Torres Roca J F, Caudell J J. The Radiosensitivity Index Predicts For Overall Survival in Glioblastoma. Oncotarget 2015:in press.
19. Creelan B, Eschrich S A, Fulp W J, Torres Roca J F. A Gene Expression Platform to Predict Benefit From Adjuvant External Beam Radiation in Resected Non-Small Lung Cancer. ASTRO; 2014; San Francisco: International Journal of Radiation Oncology Biology Physics. p. S76.
20. Fenstermacher D A, Wenham R M, Rollison D E, Dalton W S. Implementing personalized medicine in a cancer center. Cancer J 2011; 17:528-36.
21. Welsh E A, Eschrich S A, Berglund A E, Fenstermacher D A. Iterative rank-order normalization of gene expression microarray data. BMC Bioinformatics 2013; 14:153.
22. Eschrich S A, Fulp W J, Pawitan Y, et al. Validation of a radiosensitivity molecular signature in breast cancer. Clin Cancer Res 2012; 18:5134-43.
23. Fowler J F. 21 years of biologically effective dose. The British journal of radiology 2010; 83:554-68.
24. Qi X S, White J, Li X A. Is alpha/beta for breast cancer really low? Radiother Oncol 2011; 100:282-8.
25. Jeong J, Shoghi K I, Deasy J O. Modelling the interplay between hypoxia and proliferation in radiotherapy tumour response. Phys Med Biol 2013; 58:4897-919.
26. Bartelink H, Horiot J C, Poortmans P M, et al. Impact of a higher radiation dose on local control and survival in breast-conserving therapy of early breast cancer: 10-year results of the randomized boost versus no boost EORTC 22881-10882 trial. J Clin Oncol 2007; 25:3259-65.
27. Bartelink H, Maingon P, Poortmans P, et al. Whole-breast irradiation with or without a boost for patients treated with breast-conserving surgery for early breast cancer: 20-year follow-up of a randomised phase 3 trial. Lancet Oncol 2015; 16:47-56.
28. Darby S, McGale P, Correa C, et al. Effect of radiotherapy after breast-conserving surgery on 10-year recurrence and 15-year breast cancer death: meta-analysis of individual patient data for 10,801 women in 17 randomised trials. Lancet 2011; 378:1707-16.
29. Druker B J, Guilhot F, O'Brien S G, et al. Five-year follow-up of patients receiving imatinib for chronic myeloid leukemia. N Engl J Med 2006; 355:2408-17.
30. Abdulkarim B S, Cuartero J, Hanson J, Deschenes J, Lesniak D, Sabri S. Increased risk of locoregional recurrence for women with T1-2N0 triple-negative breast cancer treated with modified radical mastectomy without adjuvant radiation therapy compared with breast-conserving therapy. J Clin Oncol 2011; 29:2852-8.
31. Voduc K D, Cheang M C, Tyldesley S, Gelmon K, Nielsen T O, Kennecke H. Breast cancer subtypes and the risk of local and regional relapse. J Clin Oncol 2010; 28:1684-91.
32. Arvold N D, Taghian A G, Niemierko A, et al. Age, breast cancer subtype approximation, and local recurrence after breast-conserving therapy. J Clin Oncol 2011; 29:3885-91.
33. Lowery A J, Kell M R, Glynn R W, Kerin M J, Sweeney K J. Locoregional recurrence after breast cancer surgery: a systematic review by receptor phenotype. Breast Cancer Res Treat 2012; 133:831-41.
34. Adkins F C, Gonzalez-Angulo A M, Lei X, et al. Triple-negative breast cancer is not a contraindication for breast conservation. Ann Surg Oncol 2011; 18:3164-73.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:
1. A method of treating a subject having a tumor, comprising:
   determining a radiosensitivity index of the tumor, the radiosensitivity index being assigned from expression levels of one or more signature genes;
   deriving a subject-specific variable based on the radiosensitivity index;
   obtaining a genomic adjusted radiation dose effect value for the tumor, the genomic adjusted radiation dose effect value being predictive of tumor recurrence in the subject after treatment; and
   determining a radiation dose based on the subject-specific variable and the genomic adjusted radiation dose effect value.
2. The method of claim 1, wherein determining a radiation dose further comprises determining a radiation dose per treatment or a number of radiation treatments.
3. The method of claim 1, wherein the genomic adjusted radiation dose effect value for the tumor comprises a range of values predictive of tumor recurrence in the subject after treatment.
4. The method of claim 1, wherein the genomic adjusted radiation dose effect value for the tumor is indicative of a low chance of tumor recurrence in the subject after treatment.
5. The method of claim 1, wherein the genomic adjusted radiation dose effect value for the tumor is specific to a type of cancer.
6. The method of claim 5, wherein the type of cancer comprises breast, lung, prostate, glioblastoma, head and neck, pancreas, esophagus, or colorectal cancer.
7. The method of claim 1, further comprising determining the genomic adjusted radiation dose effect value using a univariate or multivariate analysis of genomic dose effect value and outcome for a group of subjects.
8. The method of claim 1, wherein the subject-specific variable provides a measure of the tumor's ability to accumulate radiation damage.
9. The method of claim 1, wherein the subject-specific variable is derived using a linear quadratic model for cell survival, the radiosensitivity index being approximately equal to cell survival.
10. The method of claim 1, wherein the one or more signature genes comprise at least one of Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); or Interferon regulatory factor 1 (IRF1).
11. The method of claim 1, further comprising generating a radiation treatment plan for the subject based on the determined radiation dose, wherein the radiation treatment plan indicates a number of radiation treatments and a radiation dose for each radiation treatment.
12. A system for developing a radiation therapy treatment plan for a subject having a tumor, comprising:
   a processor; and
   a memory operably coupled to the processor, the memory having computer-executable instructions stored thereon that, when executed by the processor, cause the processor to:
      determine a radiosensitivity index of the tumor, the radiosensitivity index being assigned from expression levels of one or more signature genes;
      derive a subject-specific variable based on the radiosensitivity index;
      obtain a genomic adjusted radiation dose effect value for the tumor, the genomic adjusted radiation dose effect value being predictive of tumor recurrence in the subject after treatment; and
      determine a radiation dose based on the subject-specific variable and the genomic adjusted radiation dose effect value.
13. The system of claim 12, wherein determining a radiation dose comprises determining a number of radiation treatments.
14. The system of claim 12, wherein the genomic adjusted radiation dose effect value for the tumor comprises a range of values predictive of tumor recurrence in the subject after treatment.
15. The system of claim 12, wherein the genomic adjusted radiation dose effect value for the tumor is indicative of a low chance of tumor recurrence in the subject after treatment.
16. The system of claim 12, wherein the genomic adjusted radiation dose effect value for the tumor is specific to a type of cancer.
17. The system of claim 16, wherein the type of cancer comprises breast, lung, prostate, glioblastoma, head and neck, pancreas, esophagus, or colorectal cancer.
18. The system of claim 12, wherein the memory has further computer-executable instructions stored thereon that, when executed by the processor, cause the processor to determine the genomic adjusted radiation dose effect value using a univariate or multivariate analysis of genomic dose effect value and outcome for a group of subjects.
19. The system of claim 12, wherein the subject-specific variable provides a measure of the tumor's ability to accumulate radiation damage.

20. The system of claim 12, wherein the subject-specific variable is derived using a linear quadratic model for cell survival, the radiosensitivity index being approximately equal to cell survival.

21. The system of claim 12, wherein the one or more signature genes comprise at least one of Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); or Interferon regulatory factor 1 (IRF1).

22. The system of claim 12, wherein the memory has further computer- executable instructions stored thereon that, when executed by the processor, cause the processor to generate a treatment plan for the subject based on the determined radiation dose, wherein the treatment plan indicates a number of radiation treatments and a radiation dose for each radiation treatment.

\* \* \* \* \*